United States Patent
Sunaoshi

(10) Patent No.: US 7,194,335 B2
(45) Date of Patent: Mar. 20, 2007

(54) MANIPULATOR AND ITS CONTROL APPARATUS AND METHOD

(75) Inventor: Takamitsu Sunaoshi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/270,746

(22) Filed: Nov. 10, 2005

(65) Prior Publication Data

US 2006/0069451 A1 Mar. 30, 2006

Related U.S. Application Data

(62) Division of application No. 10/813,110, filed on Mar. 31, 2004, now Pat. No. 6,993,413.

(30) Foreign Application Priority Data

Mar. 31, 2003 (JP) ............................ 2003-096819

(51) Int. Cl.
*G05B 19/18* (2006.01)
*G05B 19/418* (2006.01)
*G05B 15/00* (2006.01)
*G05B 19/39* (2006.01)
*G05B 19/408* (2006.01)
*G05B 23/02* (2006.01)
*B25J 9/10* (2006.01)

(52) U.S. Cl. ...................... 700/254; 700/248; 700/253; 700/257; 700/258; 318/568.17; 318/568.2; 318/568.22; 318/568.24; 901/49; 901/50

(58) Field of Classification Search ................... 700/3, 700/56, 57, 61, 62, 65, 66, 75, 245, 253, 700/247–250, 254, 257, 258, 262, 264; 901/3, 901/4, 6, 8, 46, 49, 50; 318/568.11, 568.13, 318/568.14, 568.16, 568.17, 568.2, 568.22, 318/568.24; 606/130
See application file for complete search history.

(56) References Cited

U.S. PATENT DOCUMENTS

| 5,047,701 | A | | 9/1991 | Takarada et al. |
| 5,134,767 | A | * | 8/1992 | Yasuda ......................... 483/7 |
| 5,777,870 | A | * | 7/1998 | Takaku et al. ................. 700/3 |
| 6,120,433 | A | | 9/2000 | Mizuno et al. |
| 6,459,926 | B1 | | 10/2002 | Nowlin et al. |

(Continued)

FOREIGN PATENT DOCUMENTS

JP   4-360777   12/1992

(Continued)

*Primary Examiner*—Crystal J. Barnes
(74) *Attorney, Agent, or Firm*—Oblon, Spivak, McClelland, Maier & Neustadt, P.C.

(57) ABSTRACT

A manipulator operative in a master/slave operative mode, comprising: a master unit commanding an operation; a slave unit having a work unit; a detector detecting the orientation of the master unit and the orientation of the slave unit; and a control device controlling the slave unit in response to the command from the master unit, wherein the control device includes: a function of determining a non-mater/slave operative mode or a master/slave operative mode; a function of calculating a difference between the orientation of the master unit and the orientation of the slave unit; and a function of comparing the absolute value of the difference with a preset reference value; and depending upon the result of the comparison, determining a normal master/slave operative mode or a transitional master/slave operative mode, in the master/slave operative mode, the transitional master/slave operative mode is a transitional mode from the non-master/slave operative mode to the master/slave operative mode.

9 Claims, 6 Drawing Sheets

U.S. PATENT DOCUMENTS

| | | |
|---|---|---|
| 6,659,939 B2 | 12/2003 | Moll et al. |
| 6,723,106 B1 * | 4/2004 | Charles et al. .............. 606/130 |
| 6,853,879 B2 | 2/2005 | Sunaoshi |
| 6,889,116 B2 | 5/2005 | Jinno |
| 6,993,413 B2 * | 1/2006 | Sunaoshi .................... 700/262 |
| 2005/0222587 A1 | 10/2005 | Jinno et al. |
| 2006/0095143 A1 * | 5/2006 | Sunaoshi ...................... 700/3 |

FOREIGN PATENT DOCUMENTS

| | | |
|---|---|---|
| JP | 8-99278 | 4/1996 |
| JP | 8-215204 | 8/1996 |
| JP | 2003-53685 | 2/2003 |
| JP | 2003340752 A | 12/2003 |
| JP | 2004299012 A | 10/2004 |

* cited by examiner

MANIPULATOR AND ITS CONTROL APPARATUS AND METHOD

CROSS-REFERENCE TO RELATED APPLICATIONS

This application is a divisional of and claims the benefit of priority under 35 USC §120 from U.S. application Ser. No. 10/813,110, filed Mar. 31, 2004 now U.S. Pat. No. 6,993,413, and is based upon and claims the benefit of priority under 35 USC §119 from prior Japanese Patent Application No. 2003-096819, filed on Mar. 31, 2003, the entire contents of which are incorporated herein by reference.

BACKGROUND OF THE INVENTION

1. Field of the Invention

The present invention relates generally to a manipulator, and its control device and method. More specifically, the invention relates to a medical manipulator operative in a master/slave mode, and its control device and method.

2. Related Background Art

In conventional laparoscope surgery such as laparoscopic cholecystectomy, an endoscope and forceps are inserted into an abdominal cavity through trocars set in small incisions made in the abdomen of a patient. Then, an operator conducts operation while watching the image acquired by the endoscope on a monitor. Since this type of operation does not need to open the abdomen, physical burden on the patient is alleviated, and the time required for recovery and discharge from the hospital after operation is greatly reduced. Therefore, its adaptation to wider fields of application is expected. Conventional laparoscope surgery, however, involves some problems. That is, the operator cannot directly observe the affected part of the patient. Additionally, there are used forceps only having an opening/closing gripper, not convenient to control and therefore unsuitable for surgery. Thus, the conventional laparoscope surgery needs high skills of operators.

To cope with these problems, it has been studied and is now being employed to furnish the forceps end with some degrees of freedom of motion so that a work unit (slave unit) at the forceps end having a plurality of degrees of freedom works in accordance with movements of a control unit (master unit) controlled by an operator to execute laparoscope surgery in a master/slave operative mode.

As one of master/slave medical manipulators, there is a remote-control device in which the master unit and the slave unit are normally located apart from each other. This is configured to set a plurality of slave arms on the patient and control positions and orientations of the medical manipulator's ends by controlling the master unit located apart from the patient. This system is complex and large-scaled, and needs high purchasing and maintenance costs. Moreover, it is not so convenient because of requiring much time to set the system ready for actual operation and being liable to interruption of operation. Furthermore, since the operator cannot attend closely to the patient during operation and is not available for quick treatment upon emergent accident, the system is insufficient from the viewpoint of safety.

There is another master/slave medical manipulator in which some of axes in the master unit and the slave unit are common axes. This is a simple, easy-to-employ, unitary medical master/slave manipulator. As compared with the foregoing remote-controlled manipulator, the operator can attend closely to the patient and directly controls the manipulator. Therefore, this unitary manipulator significantly reduces the problem of safety.

However, these medical manipulators have been developed mainly targeting their functions with affected parts to be operated or treated, and other issues remain unsolved, including how the system is easy to set in the operating room, easy for the operator to use, easy to sterilize and clean, easy to start its actual use, etc. as well as the issue of the cost.

One of problems of conventional techniques is that, if the master/slave medical manipulator is started to move from a status where the control unit (master unit) and the work unit (slave unit) do not coincide in orientation, the slave unit does not move as the user (operator) intends.

This is because, if the operator starts to control the manipulator from those both do not coincide in orientation, the operator cannot accurately recognize the difference between the orientation of the slave unit displayed on the endoscopic monitor and the orientation of the control unit and gets confused. Under the condition, the manipulator is unreliable in controllability and degrades in safety. Thus, it involves technical problems to be overcome.

To overcome those problems, there is a method of bringing the master unit into agreement with the orientation of the slave unit held stationary (Japanese Patent Laid-open No. JP-H08-215204A). This method is a diversion of a method having been employed in an industrial robot.

More specifically, in a manipulator having a detector means for detecting orientation angles of the slave portion and the master portion and a means for comparing results of their detection, while stopping the slave, the operator first controls and brings the master unit into agreement with the orientation of the slave, and thereafter starts the master/slave motion. However, this method fails to improve the controllability of the manipulator because the operator must conduct alignment of the orientations every time before starting or re-starting the master/slave motion. Moreover, since the operator must conduct the alignment for all of plural degrees of freedom of motion, it takes much time for the alignment. Furthermore, these problems cannot be disregarded also from the standpoint of quick attendance and treatment against unexpected accidents on site.

There is another method for automatically move the master unit into agreement with the orientation of the slave unit (Japanese Patent Laid-open No. JP-2002-053685). In this method, a manipulator includes a detector means for detecting orientation angles of the slave unit and the master unit and a means for sequentially comparing results of their detection. Then, the manipulator is operative in a transitional master/slave mode in which the slave is moved based on the difference between the orientation of the master unit and that of the slave unit as well as the time required for alignment of the orientations. This method removes the troublesome process of alignment, which is one of disadvantages of the foregoing method, and realizes the motion faithful to the operator's intention even during the alignment operation of orientations. However, if the alignment of orientations is started under existence of a large difference in orientation, then the distance of automatic movement of the slave unit and its time are large, and the slave unit starts moving in response to the alignment start command. Therefore, automatic motion out of the operator's intention appears saliently, and the safety issue still remains unsolved.

SUMMARY OF THE INVENTION

To overcome the problems involved in the conventional techniques discussed above, it is an object of the present invention to provide a medical manipulator enhanced in controllability and safety, which aligns the orientation of master unit and that of the slave unit without calling the operator's recognition about the process of the alignment when the operator starts controlling the master/slave medical manipulator, but does not effect automatic motions that are out of operator intention and therefore dangerous for medical use, and reflects the operator's intention to the motion of the slave unit even during the alignment operation.

According to an embodiment of the invention, there is provided a manipulator operative in a master/slave operative mode, comprising:

a master unit commanding an operation;

a slave unit having a work unit;

a detector detecting the orientation of the master unit and the orientation of the slave unit; and a control device controlling the slave unit in response to the command from the master unit, wherein the control device includes:

a function of determining a non-mater/slave operative mode or a master/slave operative mode;

a function of calculating a difference between the orientation of the master unit and the orientation of the slave unit; and a function of comparing the absolute value of the difference with a preset reference value; and depending upon the result of the comparison, determining a normal master/slave operative mode or a transitional master/slave operative mode, in said master/slave operative mode, said transitional master/slave operative mode is a transitional mode from the non-master/slave operative mode to the master/slave operative mode.

According to a another embodiment of the invention, there is provided a control device of a manipulator working in a master/slave operative mode and having a master unit for commanding an operation, a slave unit having a work unit and operative in response to a command from the master unit, and a detector unit for detecting the orientation of the master unit and the orientation of the slave unit, comprising:

a function of calculating a difference between the orientation of the master unit and the orientation of the slave unit; and a function of comparing the absolute value of the difference with a preset reference value, and switching the operative mode between a transitional master/slave operative mode and a normal master/slave operative mode depending upon the result of the comparison, the transitional master/slave operative mode being a transitional mode from a non-master/slave operative mode to the master/slave operative mode.

According to another embodiment of the invention, there is provided a method of control a manipulator working in a master/slave operative mode and having a master unit for commanding an operation, a slave unit having a work unit and operative in response to a command from the master unit, and a detector unit for detecting a difference between the orientation of the master unit and the orientation of the slave unit, comprising:

calculating a difference between the orientation of the master unit and the orientation of the slave unit; and comparing the absolute value of the difference with a preset reference value, and depending upon the result of the comparison, determining a normal master/slave operative mode or a transitional master/slave operative mode which is a transitional mode from a non-master/slave operative mode to the master/slave operative mode.

DETAILED DESCRIPTION OF THE INVENTION

Figure 1:
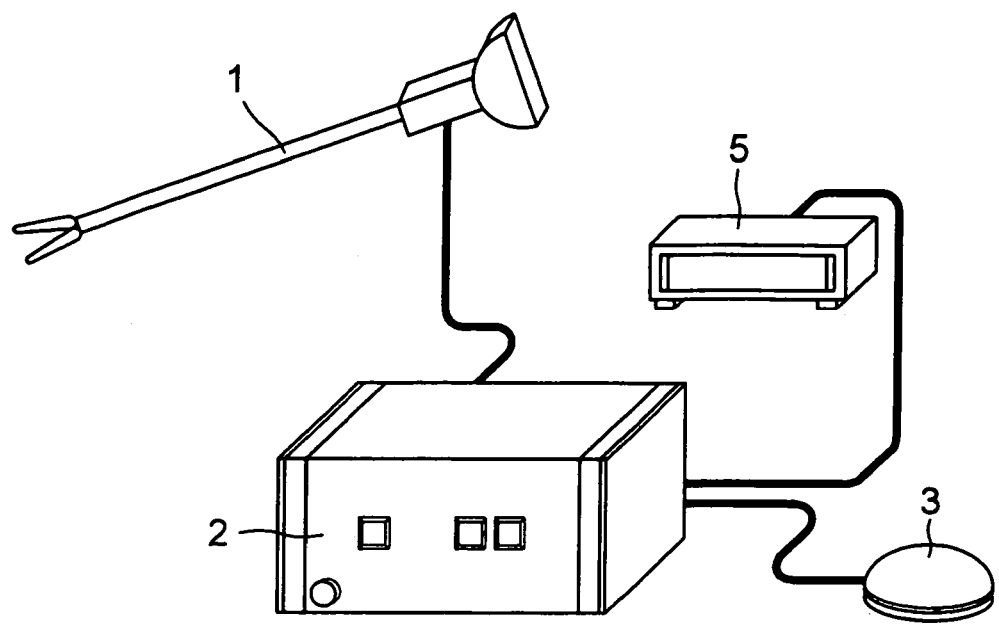
FIG. 1 is a diagram schematically showing configuration of an all-in-one medical manipulator system according to an embodiment of the present invention.

First explained is an embodiment of the present invention, taking a medical manipulator as an example. As shown in FIG. 1, medical manipulator systems, in general, are composed of a medical manipulator body 1 operative in a master/slave mode, a control device 2 for controlling and driving the medical manipulator body 1, a command input means 3 for entering a command of an operator, and an operative condition presenter 5 for presenting the operative condition of the medical manipulator.

Figure 2:
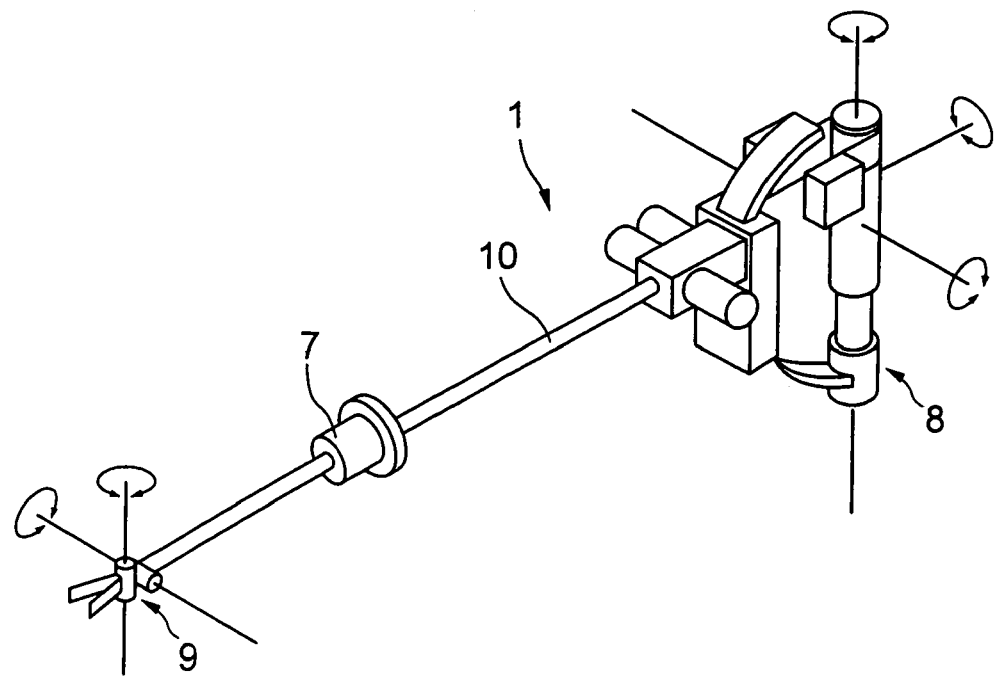
FIG. 2 is a diagram schematically showing a medical manipulator body.

The medical manipulator body 1 includes, as shown in FIG. 2, a master unit 8 controlled by a user (operator) to enter his/her command, a slave unit 9 movable in response to the movement of the master unit 8, and a connector unit 10 integrally connecting the master unit 8 and the slave unit 9. As best shown in FIG. 2, the master unit 8 is rotatable about three joint is axes. An angle sensor is attached to each joint axis of the master unit 8 to read the angular position of the joint and transmit the information about the angle of the master unit 8 moved by the operator to the control device 2 from time to time. The slave unit 9 has a degree of freedom of motion required for medical treatments, and can rotate about two joint axes to change the orientation of its end, as well as the opening and closing freedom of motion of the gripper attached to its end, which all will be effected upon corresponding commands from the operator. The slave unit 9 is powered by a motor 21, explained later, via a power transmission unit comprising a wire or rods and gears. Numeral 7 in FIG. 2 denotes a trocar.

Figure 3:
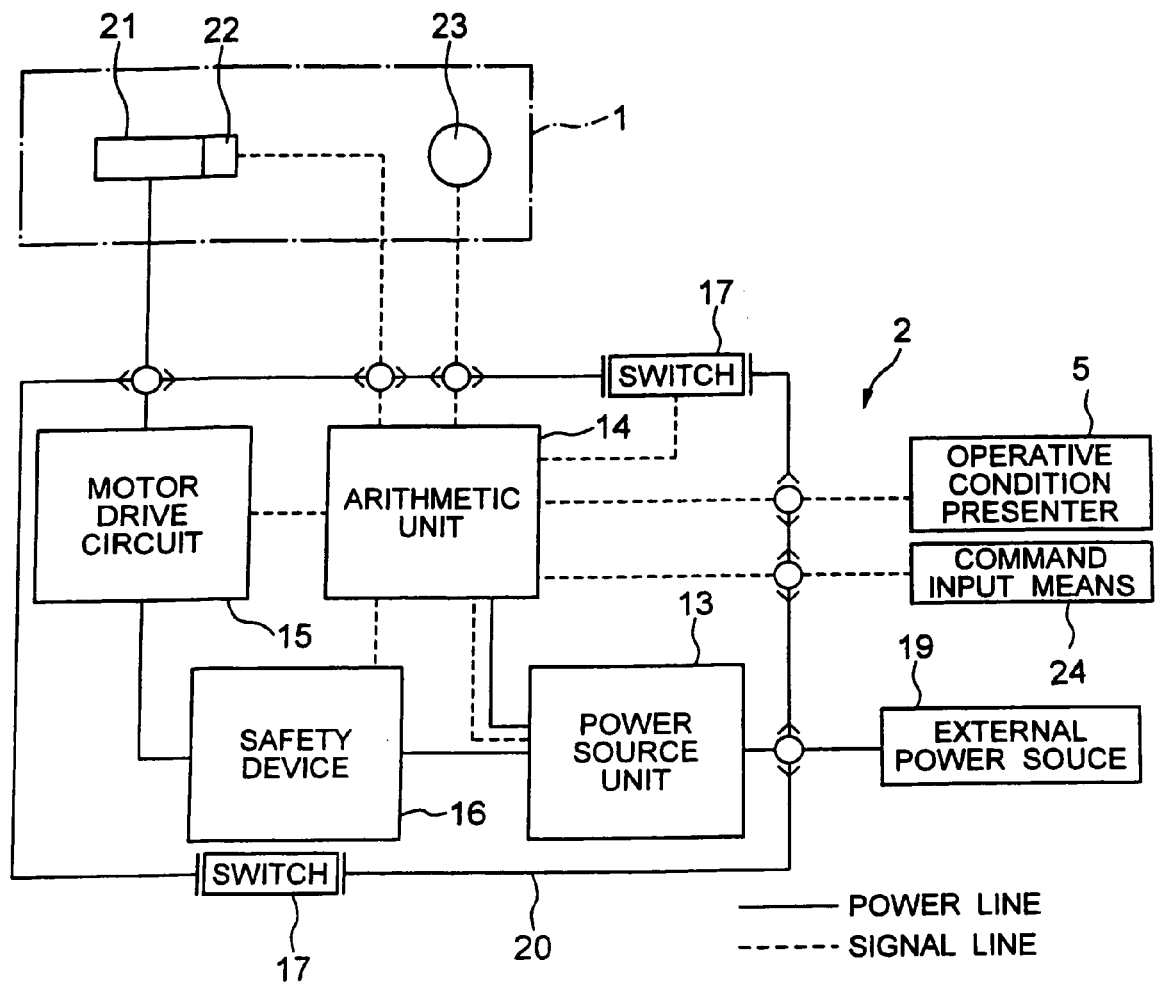
FIG. 3 is a diagram schematically showing configuration of a control device.
Figure 4:
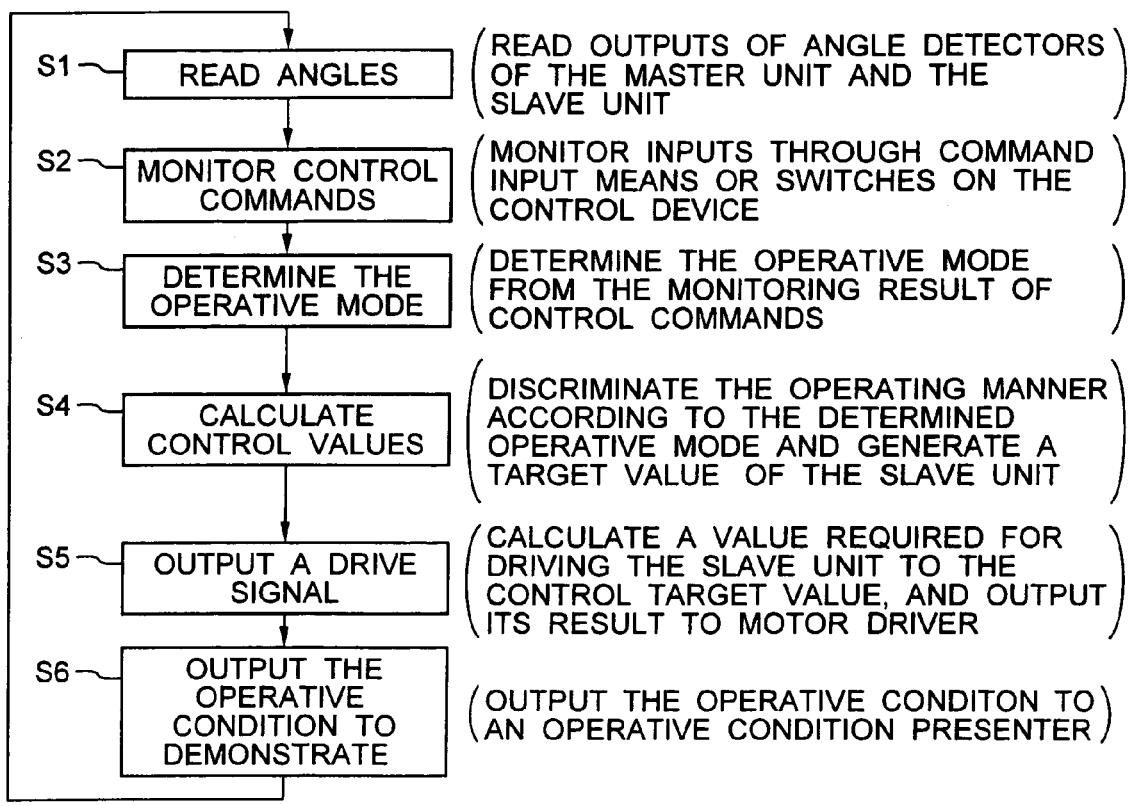
FIG. 4 is a flow chart showing the process of operations by an arithmetic unit.

The control device 2 includes, as shown in FIG. 3, a power source unit 13, arithmetic unit 14, motor drive circuit 15, safety device 16, and various switches 17. The power supply unit 13 supplies required electric power to the arithmetic unit 14 and the motor circuit from an external power source 19 via a transformer. The arithmetic unit 14 includes a CPU, storage device, logic circuit and I/O interface, and has the function to read the angular position of the master unit 8 with an angle detector 23 to generate a control target value of the motor 21 for driving the slave unit 9 and the function to acquire information from an angle detector 22 for measuring the angular position of the motor 21, then comparing it with the control target value of the motor 21 and calculating the motor command input to remove the difference. Additionally, the arithmetic unit 14 monitors signals input through various kinds of switches 17, etc. and executes arithmetic calculation for controlling pursuant to a predetermined program. The arithmetic unit 14 repeats these operations in a predetermined control period as shown in FIG. 4. The motor drive circuit 15 is a circuit for outputting power to the motor 21 in response to entry of a command from the arithmetic unit 14. The safety device 16 is provided to interrupt the power to the medical manipulator body 1 and immediately stop the movement of the body 1 upon occurrence of any irregularity in the arithmetic period of the arithmetic unit 14, any irregularity in the motor drive circuit 15 or emergency shutdown command. The switches 17 are provided in a control device housing 20, and are used for commanding changeover of the operative condition of the medical manipulator and for switching the power.

A command input means 3 (FIG. 1) is prepared for direct control by an operator to smoothly execute his/her command to start or terminate activation of the medical manipulator or change its operative condition. The command input means 3 is preferably a foot switch to free the operator's hands. Alternatively, the command input means 3 may be controlled by voice commands or may be attached on the medical manipulator body.

The operative condition presenter 5 presents the operative condition of the medical manipulator body 1 to allow the operator or assistant of the surgical operation to easily confirm how the manipulator is actually controlled and to thereby increase the safety of the operation. The operative condition presenter 5 is preferably located near the endoscope monitor so that the operator can catch the representation within his/her most natural field of view.

Behaviors of the arithmetic unit 14 shown in FIG. 4 are briefly explained from one step to another. The arithmetic unit 14 reads outputs of the angle detectors 22, 23 of the master unit 8 and the slave unit 9 (S1). Thereafter, it monitors the inputs to the command input means 24 or to the switches 17 attached to the command input means 3 (S2). Then, it judges the operative mode of the manipulator based on the result of the monitoring (S3), and next discriminates the activation method and generates a slave unit target value according to the judged operative mode (S4). After that, it calculates the control value for driving the slave unit 9 pursuant to the target value and outputs its result to the motor driver (motor drive circuit 15) (S5). Thereafter, it outputs the operative condition to the operative condition presenter 5 (S6).

If the medical manipulator body 1 comprises the master unit 8 and the slave unit 9 located apart from each other without the connector unit, this is a remote-controlled medical manipulator. In this case, the manipulator is operative in the master/slave mode by data communication between control devices associated with the master unit 8 and the slave unit 9 respectively.

Figure 5:
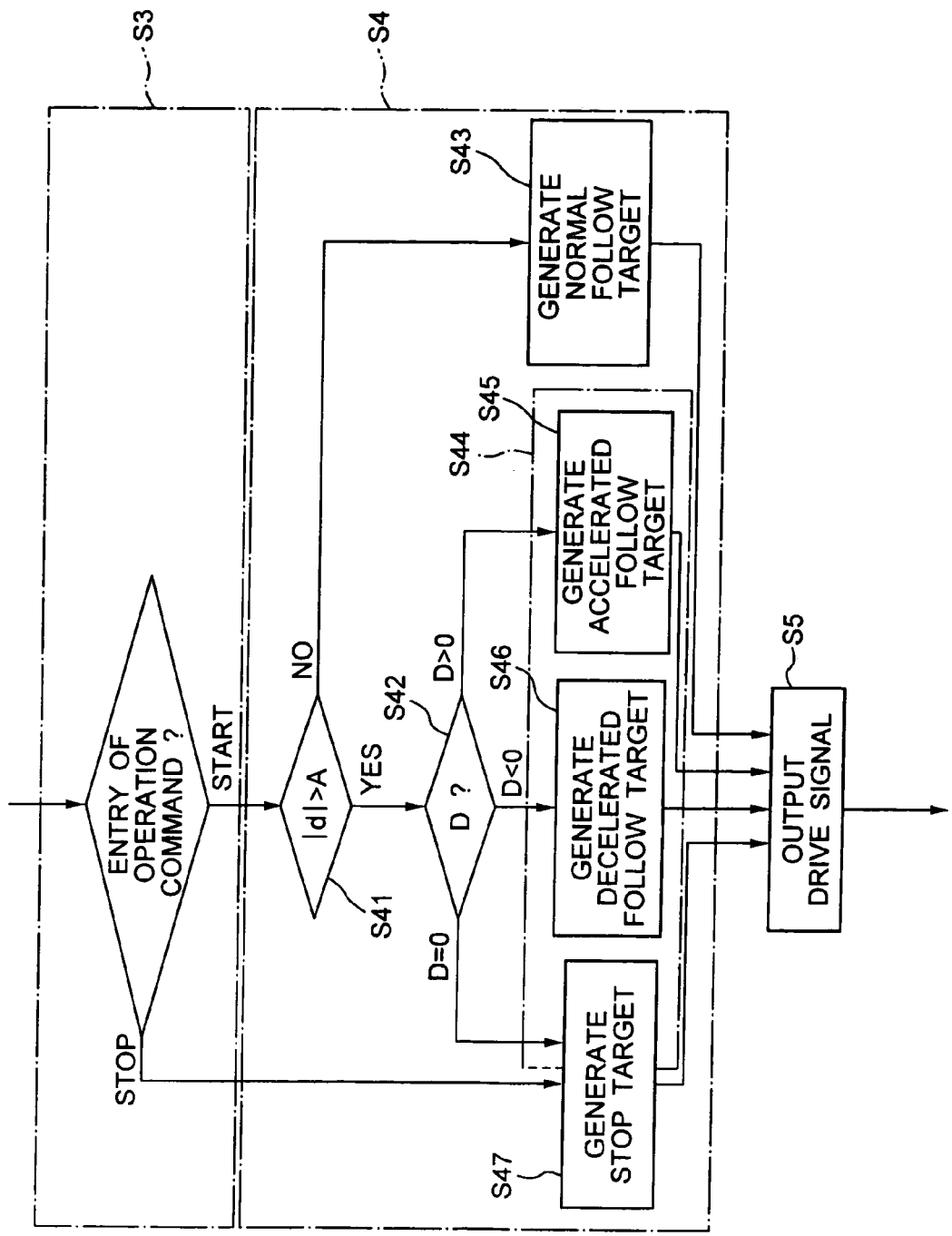
FIG. 5 is a flow chart explaining the process of judging the operative mode in the process of operations by the arithmetic unit.

Next explained are procedures for starting a master/slave operation with reference to FIG. 5. When the control device 2 is powered, the power is transmitted to the arithmetic unit 14 and the medical manipulator body 1, and the arithmetic unit 14 can read information from individual angle sensors 22, 23. In most case, just when the manipulator is powered, angular positions (orientations) of the master unit 8 and the slave unit 9 do not agree until some kind of control is done. In addition, the slave unit 9 remains in the initial orientation. The arithmetic unit 14 monitors entry of an operation start command from the operator and monitors angular positions of the master unit 8 and the slave unit 9, from time to time irrespectively of the operative mode of the manipulator (S3). The arithmetic unit 14 calculates the difference d between the angle $\theta_s$ of the slave unit 9 and the angle $\theta_m$ of the master unit 8 from Equation (1).

$$d = \theta_m - \theta_s \tag{1}$$

The operator enters a command for activating the manipulator in the master/slave operative mode to the arithmetic unit through the command input means 3 or switches 17 of the control device 2. The arithmetic unit 14 acknowledges entry of the master/slave motion start command, and compares the difference d calculated by Equation (1) with a preset master/slave motion reference value A (S41). If the result of the comparison satisfies Equation (2), then the arithmetic unit 14 sets the manipulator in a transitional master/slave operative mode (S42).

$$|d| > A \tag{2}$$

If the result of the comparison does not satisfy Equation (2), it means that the difference between the angular position of the master unit 8 and that of the slave unit 9 is very small. Then, the arithmetic unit 14 sets the manipulator in the normal master/slave operative mode (S43). Although it is ideal that the value of d is zero in the normal master/slave operative mode, since the angles and their reading intervals are discrete, it is quite rare to observe that the master unit 8 and the slave unit 9 completely agree in angular position (orientation). Therefore, if the zero difference is pursued, then the change too the normal master/slave operative mode will not be attained for a long time even though the master unit 8 and the slave unit 9 substantially agree in angular position. Since acceptable controllability of the manipulator is assured when the difference in orientation between the master unit 8 and the slave unit 9 is nearly zero, although not purely zero, the constant A is introduced for practical application.

The transitional master/slave operative mode (S44) is a process for the change from the non-master/slave operative mode, such as the stop mode, to the normal master/slave operative mode, and the operator can control the manipulator in this mode with the same feeling as he/she will have in the master/slave operative mode.

In this transitional master/slave operative mode, the arithmetic unit 14 defines the relation between the time difference $\Delta\theta_s$ of the target value of the slave unit 9 and the time difference $\Delta\theta_m$ of the orientation of the master unit 8 by Equation (3) using a parameter $\alpha$.

$$\Delta\theta_s = \alpha \Delta\theta_m \tag{3}$$

Here is explained how to determine the parameter $\alpha$ in Equation (3) in the transitional master/slave operative mode (S44), depending upon the sign of the time difference $\Delta\theta_m$ of the orientation of the master unit 8 and the sign of the angular difference d between the master unit 8 and the slave unit 9. Whether the signs of these values are identical or opposite can be judged from the sign of D shown in Equation (4). If D is positive, both signs are equal. If the sign of D is negative, both signs are opposite.

$$D = \Delta\theta_m \times d \tag{4}$$

When D>0, that is, when the sign of the time difference of the orientation of the master unit 8 is equal to the sign of the angular difference between the master unit 8 and the slave unit 9, it means that the operator controls the orientation of the master unit 8 in a direction away from the current orientation of the slave unit 9. In this case, by determining the parameter α to satisfy Equation (5), it is possible to generate an orientation target value of the slave unit 9 so that the orientation of the slave unit 9 catches up with the orientation of the master unit (generation of the accelerated follow target) (S45).

$$\alpha > 1 \quad (5)$$

When D<0, that is, when the sign of the time difference of the orientation of the master unit 8 is different from the sign of the angular difference between the master unit 8 and the slave unit 9, it means that the operator controls the orientation of the master unit 8 in a direction toward the current orientation of the slave unit 9. In this case, by determining the parameter α to satisfy Equation (6), it is possible to generate an orientation target value of the slave unit 9 so that the orientation of the master unit catches up with the orientation of the slave unit 9 (generation of the decelerated follow target) (S46).

$$0 \leq \alpha < 1 \quad (6)$$

The transitional master/slave operative mode (S44) is brought about in one of the above-mentioned cases. In any of these cases, once the operator stops the master unit 8, the slave unit 9 also stops (generation of the stop target) (S47) because the time difference $\Delta\theta_s$ of the target value of the slave unit becomes zero irrespectively of the value of the parameter α. That is, even in the transitional master/slave operative mode (S44), if the operator wants to stop the slave unit 9 in a desired orientation, he/she may only stop the control of the master unit 8 and can control the manipulator intuitively.

The arithmetic unit 14 monitors the magnitude of d expressed in Equation (1) in each control cycle or in predetermined intervals. When d=0, there is no angular difference between the master unit 8 and the slave unit 9, and these units agree in orientation. Thus, it changes the operative mode of the manipulator to the normal master/slave operative mode.

Heretofore, for easier understanding, explanation has been made assuming that the normal master slave operative mode is the operative mode equally setting the moving amount $\theta_{mq}$ of the master unit and the moving amount $\theta_{sq}$ of the slave unit following to the typical master/slave mode. Next, however, another extensive way of setting the parameter α will be explained, which will cope with various kinds of master/slave operative modes.

In the normal master/slave operation, the moving ratio may be changed between the master unit 8 and the slave unit 9 in order to enhance the controllability. For example, movement of the slave unit 9 may be a half of the movement of master unit. This is a technique used when a minute movement of the slave unit 9 is required and the master unit 8 is difficult to control for the same scale of minute movement. In contrast, movement of the slave unit 9 may be a double of the movement of the master unit 8 to reduce the operator's amount of movement and thereby alleviate the operator's load. As such, in the normal master/slave operative mode, the movement ratio may be changed as shown in Equation (7).

$$\Delta\theta_s = \beta \Delta\theta_m \quad (7)$$

In case of a medical manipulator having this kind of normal master/slave operative mode, the transitional master/slave operative mode can be defined as Equation (8) converted from Equation (3).

$$\Delta\theta_s = \alpha^*(\beta \Delta\theta_m) \quad (8)$$

Combining Equation (3) and Equation (8), relation between the slave target value and the master unit orientation in the transitional master/slave operative mode can be defined by Equation (9).

$$\Delta\theta_s = \alpha_{ext} \Delta\theta_m \quad (9)$$

Then, the parameter $\alpha_{ext}$ can be expressed by using the parameter β determined by the movement ratio in the normal master/slave operation or the operator's intention as follows.

$$0 \leq \alpha_{ext} \leq \beta (D<0) \quad (10)$$

$$\alpha_{ext} \geq \beta (D>0) \quad (11)$$

Figure 6:
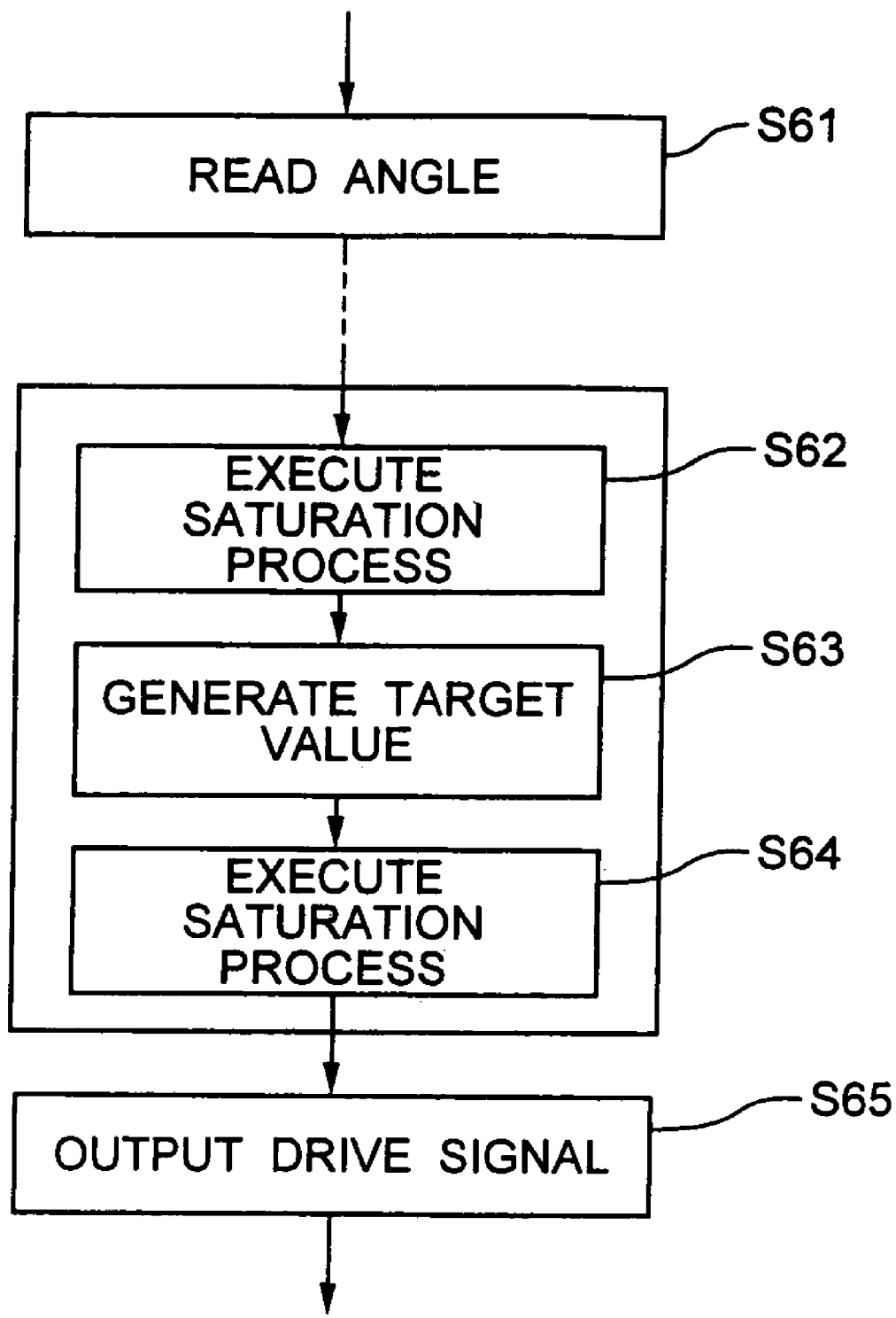
FIG. 6 is a diagram showing the sequence of saturation processing used in a conventional master/slave operative mode.
Figure 7:
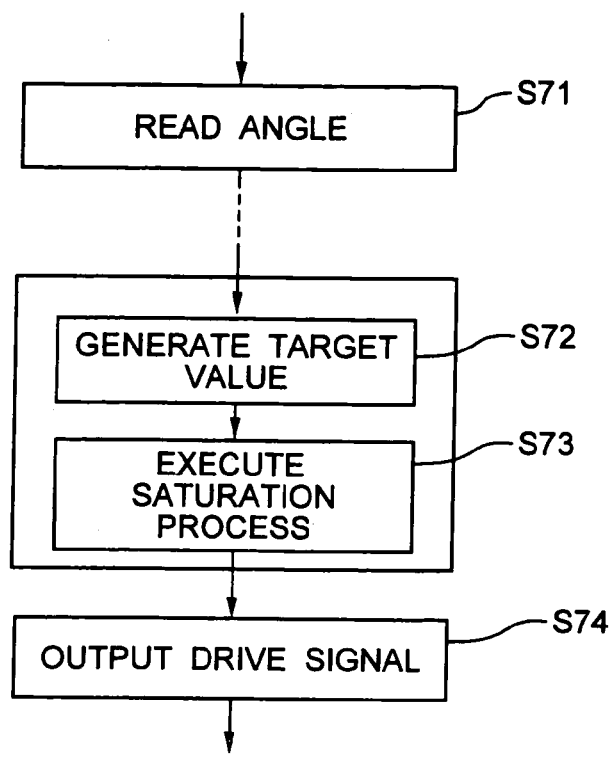
FIG. 7 is a diagram showing the sequence of saturation processing used in a transitional master/slave operative mode.
Figure 8:
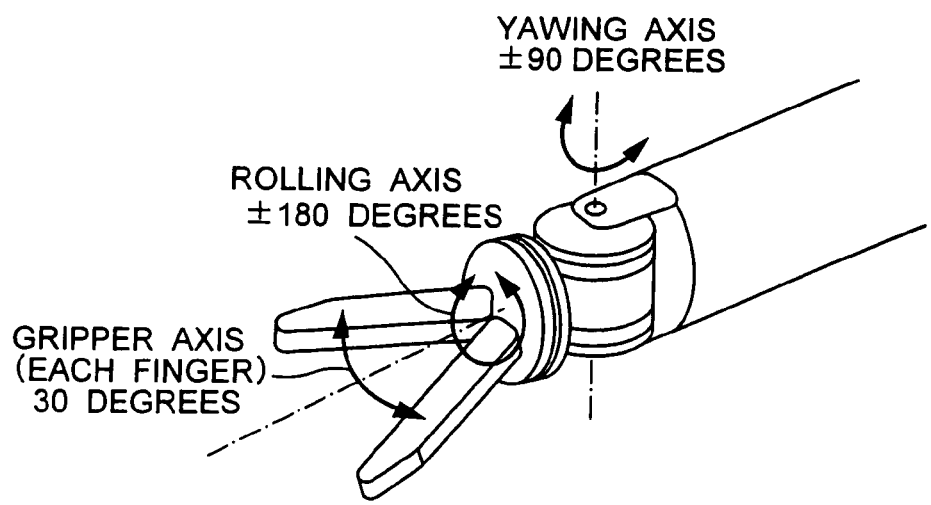
FIG. 8 is a diagram showing the slave unit end to illustrate an arrangement for a degree of freedom of motion of a medical manipulator.

Medical manipulators having the typical master/slave operative mode, in general, are configured to reserve a slightly larger range of movement for the master unit 8 than that of the slave unit 9 (S63) to read the angle of the master unit 8 (S61), then generate the target value of the slave unit 9 after saturation processing of the angle (S62), again execute saturation processing and arithmetic operation (S64), and output a drive signal (S65) as shown in FIG. 6. Since the transitional master/slave operative mode enables pseudo master/slave operation even under a difference in orientation between the master unit 8 and the slave unit 9, the controllability of the manipulator can be improved by adding the function to make use of values normally discarded. In the normal master/slave operative mode and the transitional master/slave operative mode, if the arithmetic unit 14 is configured to assume both the determination whether to subject a value from the master unit 8 to saturation processing or not, i.e. the determination whether to discard or use output values responsive to the orientation of the master unit in the non-sensitive region in the normal master/save operative mode, and sorting processing based on the determination, then the structure becomes complicate. Therefore, as shown in FIG. 7, here is provided an arithmetic process of reading the angle of the master unit 8 (S71), generating a target value suitable for the operative mode and the operating manner (S72), thereafter execute saturation processing (S73) and outputs the drive signal (S74). With this function, excessive drive power beyond the operative range of the slave unit 9 is no more output not only in the normal aster/slave operative mode but also in the transitional master/slave operative mode. Thus, the manipulator is enhanced in safety. Since the master unit 8 can be controlled by the operator as desired, the control speed can be optionally determined as well. Actually, however, there are limit values for the drive speed of the motor for driving the slave unit 9 and for the operative speed of the transmission system. Therefore, saturation processing is employed to assure that excessive drive force beyond the limitative value of the operation speed is not exerted.

Thus, the transitional master/slave operative mode in the embodiment of the invention satisfies Equation (9), Equation (10) and Equation (11). If it is desired to move the master unit 8 and the slave unit 9 in opposite directions, the sign of the parameter α may be inverted. The value of the parameter α should be selected within the range satisfying those equations.

EXAMPLE 1

Here is explained an application of determining the parameter α in Equation (3). In a medical manipulator having three degrees of freedom of motion including the freedom about the gripper axis in addition to the freedom about the yawing axis and the rolling axis, as shown in FIG.

8, the slave unit of the manipulator have the movable ranges of ±90 degrees about the yawing axis, ±180 degrees about the rolling axis, and 30 degrees of opening angle (of each finger) about the gripper axis (the gripper is shut at 0 degree). The parameter β of the normal master/slave mode is determined as Equation (12). This corresponds to β=1.

$$\begin{pmatrix} \Delta\theta_{s-yaw} \\ \Delta\theta_{S-roll} \\ \Delta\theta_{s-grip} \end{pmatrix} = \begin{pmatrix} 1 & 0 & 0 \\ 0 & 1 & 0 \\ 0 & 0 & 1 \end{pmatrix} \begin{pmatrix} \Delta\theta_{m-yaw} \\ \Delta\theta_{m-roll} \\ \Delta\theta_{m-grip} \end{pmatrix} \quad (12)$$

Since this medical manipulator has a relatively large ovable range about the rolling axis than those about the other two axes, the parameter in the transitional master/slave operative mode was determined as Equation (13) and Equation (14).

When $\Delta\theta_m$ and d have the same sign, $$\alpha = \begin{pmatrix} 2 & 0 & 0 \\ 0 & 3 & 0 \\ 0 & 0 & 2 \end{pmatrix} \quad (13)$$

When $\Delta\theta_m$ and d have the opposite signs, $$\alpha = \begin{pmatrix} 1/2 & 0 & 0 \\ 0 & 1/3 & 0 \\ 0 & 0 & 1/2 \end{pmatrix} \quad (14)$$

By changing the value of the parameter α for each axis to be controlled and changing the motion speed about each axis in the transitional master/slave operative mode, the manipulator can be adjusted in controllability. As to adjustment of the parameter, the manipulator may be configured to permit the operator to change the setting of the parameter as desired through interface prepared in the medical manipulator system, such as a terminal externally connected to the control deice, for example. In this case, the arithmetic unit will read the new setting value and control the work unit accordingly. Thus, the medical manipulator permitting adjustment in the operator's favor can be realized.

EXAMPLE 2

In case much importance is given to the response to controls also in the transitional master/slave operative mode to realize alignment of orientations in the transitional master/slave operative mode without reducing the speed lower than that of the normal master/slave operative mode, the value of $\alpha_{ext}$ under D<0 is set to β to enable alignment of orientations without using the decelerated follow. In this manner, while the master unit moves closer to the slave unit (D<0), the speed does not decrease although the difference in orientation is not removed. While the master unit moves away from the slave unit (D>0), the difference in orientation is removed.

In contrast, in case much importance is given to safety and an increase of the speed should be prevented, the value of $\alpha_{ext}$ under D>0 is set to β because the accelerated follow is desired to cancel in the transitional master/slave operative mode. In this case, the difference in orientation is not removed, but an increase of the speed does not occur. Instead, $\alpha_{ext}$ is determined to remove the difference in orientation when D<0.

If the value of $\alpha_{ext}$ under D<0 is always β regardless of the sign of D, this is the case where the slave unit moves relative to the movement of the master unit while the difference d remains unchanged. This mode of operation is usable when the configuration of the master unit is different from the configuration of the slave unit, e.g., when it is controlled through a relative input device such as switches or levers.

In other words, the manipulator is configured to include the function to employ or discard the operating manner in the transitional master/slave operative mode.

EXAMPLE 3

Here is explained an application of an embodiment of the invention for resuming the master/slave operation. There is a method of restricting movements about any particular one of the axes of the slave unit in the master/slave operative mode in order to enhance the controllability. The condition restricting a movement about the particular axis corresponds to the condition where the particular axis of the master/slave operative axes is set in a non-master/slave operative mode. The embodiment of the invention is applicable also upon returning to the normal master/slave operative mode. Regarding the release of the restriction as the start command of the master/slave operative mode, transitional master/slave operation may be conducted regarding the axis heretofore restricted.

EXAMPLE 4

During controls of a medical manipulator in the master/slave operative mode, the actual orientation of the slave unit may deviate from the target value produced for the slave unit due to a suture thread entangling on a joint of the manipulator or an excessive load to the manipulator end, for example. Upon these occasions, the medical manipulator has to demonstrate an alarm signal to the operator's awareness by representation on an operative condition presenter, for example, and simultaneously remove the irregular condition to recover the safety of the surgical operation immediately. In this case, the arithmetic unit may be configured to recognize the alarm signal and previously store the recovery procedure to remove the difference in orientation produced between the slave unit and the master unit. Then, it is possible to restore the normal master/slave operation quickly by using the transitional master/slave operation according to the invention to resume the surgical operation quickly and safely.

EXAMPLE 5

Upon changing a non-master/salve operative mode to the master/slave mode, automatic alignment of orientations is better for controllability provided it is surely safe. For example, before the slave is inserted into the patient's body, there may be nothing to hit in its movable range. The medical manipulator may be provided with input switches allowing the operator to distinctively command the alignment of orientations by automatic operation (for example, Japanese Patent Laid-open JP-2001-243434A (here is called automatic transitional operation) and the alignment according to the invention, respectively, so that the arithmetic unit reads the input in its process of monitoring operation commands and may execute the switching in its operation judging process. In this manner, it is possible to realize a medical manipulator having the function of switching the automatic transitional operation and the transitional master/slave operation for alignment of orientations, and therefore enhanced in controllability. If the arithmetic unit is configured to conduct the operation command monitoring process and the operation judging process for each axis, these methods of alignment of orientations can be executed for each axis.

EXAMPLE 6

The master unit may include power torque sensors associated with the axes to transmit the force or torque as information from the master unit to the arithmetic unit. If the arithmetic unit has the function of converting the information on the force or torque to information on position or speed, the transitional master/slave operative mode is applicable.

As described above, according to the invention, it is possible to provide a medical manipulator enhanced in controllability and safety.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

What is claimed is:

1. A manipulator operative in a master/slave operative mode, comprising:
   a master unit commanding an operation;
   a slave unit having a work unit;
   a detector detecting the orientation of the master unit and the orientation of the slave unit; and
   a control device controlling the slave unit in response to a command from the master unit,
   wherein the control device includes:
   a first function of determining a non-master/slave operative mode or a master/slave operative mode;
   a second function of calculating a difference between the orientation of the master unit and the orientation of the slave unit;
   a third function of comparing the absolute value of the difference with a preset reference value, and depending upon the result of the comparison, determining a normal master/slave operative mode or a transitional master/slave operative mode, in said master/slave operative mode, said transitional master/slave operative mode being a transitional mode from the non-master/slave operative mode to the master/slave operative mode;
   a fourth function of restricting the operation of the slave unit in said master/slave operative mode to set the manipulator in the non-master/slave operative mode; and
   a fifth function of performing the first to third functions in response to a restriction release command, and, after performing the fourth function, setting the manipulator in said transitional master/slave operative mode.

2. The manipulator according to claim 1, wherein a restriction of a movement of the slave unit is conducted on arbitrarily selected one or more operative axes.

3. A control device of a manipulator working in a master/slave operative mode and having a master unit for commanding an operation, a slave unit having a work unit and operative in response to a command from the master unit, and a detector unit for detecting the orientation of the master unit and the orientation of the slave unit, comprising:
   a first function of determining a non-master/slave operative mode or a master/slave operative mode;
   a second function of calculating a difference between the orientation of the master unit and the orientation of the slave unit;
   a third function of comparing the absolute value of the difference with a preset reference value, and depending upon the result of the comparison, determining a normal master/slave operative mode or a transitional master/slave operative mode in said master/slave operative mode, said transitional master/slave operative mode being a transitional mode from the non-master/slave operative mode to the master/slave operative mode,
   a fourth function of restricting the operation of the slave unit in said master/slave operative mode to set the manipulator in the non-master/slave operative mode; and
   a fifth function of performing the first to third functions in response to a release command of the restriction, and, after performing the fourth function, setting the manipulator in said transitional master/slave operation mode.

4. The manipulator according to claim 3, wherein a restriction of a movement of the slave unit is conducted on arbitrarily selected one or more operative axes.

5. A method of controlling a manipulator working in a master/slave operative mode and having a master unit for commanding an operation, a slave unit having a work unit and operative in response to a command from the master unit, and a detector unit for detecting a difference between the orientation of the master unit and the orientation of the slave unit, comprising:
   determining, as a first function, a non-master/slave operative mode or a master/slave operative mode;
   calculating, as a second function, a difference between the orientation of the master unit and the orientation of the slave unit;
   comparing, as a third function, the absolute value of the difference with a preset reference value; and depending upon the result of the comparison, determining a normal master/slave operative mode or a transitional master/slave operative mode in said master/slave operative mode, said transitional master/slave operative mode being a transitional mode from the non-master/slave operative mode to the master/slave operative mode,
   restricting, as a fourth function, the operation of the slave unit in said master/slave operative mode to set the manipulator in the non-master/slave operative mode; and
   performing, as a fifth function, the first to third functions in response to a restriction release command, and, after performing the fourth function, setting the manipulator in said transitional master/slave operation mode.

6. The manipulator according to claim 5, wherein a restriction of a movement of the slave unit is conducted on arbitrarily selected one or more operative axes.

7. A manipulator operative in a master/slave operative mode, comprising:
   a master unit commanding an operation;
   a slave unit having a work unit;
   a detector detecting the orientation of the master unit and the orientation of the slave unit; and
   a control device controlling the slave unit in response to the command from the master unit, wherein the control device includes:

a first function of determining a non-master/slave operative mode or a master/slave operative mode;

a second function of calculating a difference between the orientation of the master unit and the orientation of the slave unit;

a third function of comparing the absolute value of the difference with a preset reference value, and depending upon the result of the comparison, determining a normal master/slave operative mode or a transitional master/slave operative mode, in said master/slave operative mode, said transitional master/slave operative mode being a transitional mode from the non-master/slave operative mode to the master/slave operative mode;

a fourth function of generating an alarm signal when there is a difference between a target value of the orientation of the slave unit and a detecting value of the orientation of the slave unit in the master/slave operative mode after performing the first to third functions; and a fifth function of setting a new orientation value to be targeted of the slave unit based on a command issued after recognizing the alarm signal, and then by performing the first to third functions, setting a mode as the transitional master/slave operative mode in order to remove a difference between a current orientation value of the master unit and the new orientation value of the slave unit.

8. A control device of a manipulator working in a master/slave operative mode and having a master unit for commanding an operation, a slave unit having a work unit and operative in response to a command from the master unit, and a detector unit for detecting the orientation of the master unit and the orientation of the slave unit, comprising:

a first function of determining a non-master/slave operative mode or a master/slave operative mode;

a second function of calculating a difference between the orientation of the master unit and the orientation of the slave unit;

a third function of comparing the absolute value of the difference with a preset reference value, and depending upon the result of the comparison, determining a normal master/slave operative mode or a transitional master/slave operative mode in said master/slave operative mode, said transitional master/slave operative mode being a transitional mode from the non-master/slave operative mode to the master/slave operative mode, a fourth function of generating an alarm signal when there is a difference between a target value of the orientation of the slave unit and a detecting value of the orientation of the slave unit in the master/slave operative mode after performing the first to third functions; and a fifth function of setting a new orientation value to be targeted of the slave unit based on a command issued after recognizing the alarm signal, and then by performing the first to third functions, setting a mode as the transitional master/slave operative mode in order to remove a difference between a current orientation value of the master unit and the new orientation value of the slave unit.

9. A method of controlling a manipulator working in a master/slave operative mode and having a master unit for commanding an operation, a slave unit having a work unit and operative in response to a command from the master unit, and a detector unit for detecting a difference between the orientation of the master unit and the orientation of the slave unit, comprising:

determining, as a first function, a non-master/slave operative mode or a master/slave operative mode;

calculating, as a second function, a difference between the orientation of the master unit and the orientation of the slave unit;

comparing, as a third function, the absolute value of the difference with a preset reference value, and depending upon the result of the comparison, determining a normal master/slave operative mode or a transitional master/slave operative mode in said master/slave operative mode, said transitional master/slave operative mode being a transitional mode from the non-master/slave operative mode to the master/slave operative mode, generating, as a fourth performance, an alarm signal when there is a difference between a target value of the orientation of the slave unit and a detecting value of the orientation of the slave unit in the master/slave operative mode after performing the first to third functions; and setting, as a fifth performance, a new orientation value to be targeted of the slave unit based on a command issued after recognizing the alarm signal, and then by performing the first to third functions, setting a mode as the transitional master/slave operative mode in order to remove a difference between a current orientation value of the master unit and the new orientation value of the slave unit.

* * * * *